United States Patent [19]

Spielvogel et al.

[11] Patent Number: 4,855,493
[45] Date of Patent: Aug. 8, 1989

[54] PHARMACOLOGICAL ACTIVE AMINE-CARBOXYBORANES

[75] Inventors: Bernard F. Spielvogel, Raleigh; Andrew T. McPhail, Durham; Iris H. Hall, Chapel Hill, all of N.C.

[73] Assignee: The United States of America, as represented by the Secretary of the Army, Washington, D.C.

[21] Appl. No.: 882,562

[22] Filed: Jul. 7, 1986

Related U.S. Application Data

[63] Continuation-in-part of Ser. No. 106,416, Dec. 21, 1979, abandoned, Continuation-in-part of Ser. No. 68,356, Aug. 21, 1979, Pat. No. 4,312,989.

[51] Int. Cl.$^4$ ............................................ C07C 101/00
[52] U.S. Cl. ..................................... 562/575; 562/553
[58] Field of Search .............................. 562/575, 553

[56] References Cited

U.S. PATENT DOCUMENTS 4,312,989  1/1982  Spielvogel ........................... 546/13

OTHER PUBLICATIONS

Mar., "Advanced Organic Chemistry, " p. 331–332, (1968).
Hall, J. Phar. Sci. 68, pp. 685–688, (1979).
Spielvogel, J. Am. Chem. Soc., 98, pp. 5702–5703, (1976).

*Primary Examiner*—Michael L. Shippen
*Attorney, Agent, or Firm*—Werten F. W. Bellamy; Anthony T. Lane

[57] ABSTRACT

Amine-carboxyboranes (boron analogues of amino acids) which demonstrate significant antitumor and antihyperlipidemic (cholesterol and /or triglyceride lowering) activities are disclosed.

5 Claims, No Drawings

PHARMACOLOGICAL ACTIVE AMINE-CARBOXYBORANES

CROSS REFERENCE

This application is a continuation-in-part of U.S. patent application Ser. No. 106,416, filed Dec. 21, 1979, now abandoned, which in turn is a continuation-in-part of U.S. patent application Ser. No. 68,356, filed Aug. 21, 1979, now U.S. Pat. No. 4,312,989, issued Jan. 26, 1982.

BACKGROUND OF THE INVENTION

All publications or patents mentioned in this specification are herein incorporated by reference.

1. Field of the Invention

This invention relates broadly to a class of systemically-administered compounds as antitumor and antihyperlipidemic agents.

Current research investigations for compounds having desirable biological activities and use in cancer chemotherapy treatments reveal the need for compounds with minimal toxicity and increased biological activity. The use of boron compounds in neutron-capture therapy was suggested as early as 1936 by G. I. Locher, *American Journal*, Vol. 36, page 1 (1936). The rationale for this therapy, now quite familiar to boron chemists, rests upon the fact that $10_B$ and thermal neutrons result in a nuclear reaction capable of destroying cells. One very important requirement for utilization of this approach is a large concentration differential of $10_B$ between the neoplasm and normal tissue so that only the tumor is destroyed. Included in the neutron-capture therapy approach is the concept, advanced by A. H. Soloway, *Progress In Boron Chemistry*, Vol. 1, The MacMillan Company, New York, 1964, Chapter 4, of preparing antimetabolites or other carcinostatic agents containing boron for a possible two-fold attack on a neoplasm. Thus, direct inhibition of tumor growth by the boron compound could be coupled with selective incorporation of the compound into thee neoplasm with concomitant use of the neutron-capture therapy.

SUMMARY OF THE INVENTION

According to this invention, there is provided novel amine-carboxyborane compounds which exhibit significant antihyperlipidemic (cholesterol and/or triglyceride lowering) and antitumor activity. More specifically, amine-carboxyboranes depicted by the chemical formula $R_1R_2NHH_2BC(O)OH$ wherein $R_1$ and $R_2$ are selected from the group consisting essentially of hydrogen, methyl, ethyl, propyl, i-propyl, t-butyl, sec-butyl, and n-butyl, or when $R_1$ is methyl, or hydrogen then $R_2$ can be an alkyl group selected from the group consisting essentially of methyl, ethyl, n-propyl, i-propyl, n-butyl, t-butyl, sec-butyl, pentyl, hexyl, heptyl, octyl, nonyl, decyl, undecyl, dodecyl, tridecyl, tetradecyl, pentadecyl, hexadecyl and octadecyl have been shown to exhibit significant antihyperlipidemic and antitumor activity.

The novel process described herein for the preparation of compounds of formula $R_1R_2NHBH_2CO_2H$ give good yields of materials which can be readily recrystallized to give high purity crystalline samples. Elemental analyses indicates a uniform composition of the samples. When a single crystal is used for crystal structure analysis, only consistent reliable results will be obtained when the crystal is of high purity, i.e. identical molecules of the substance pack in a regular fashion giving rise to crystallographic planes from which diffraction of the x-rays takes place. Thus a successful single crystal x-ray structure determination gives the detailed geometry of the molecules in the crystals and unequivocally confirms the purity of the substance. The process for the preparation by amine displacement reaction of a compound of the formula $R_1R_2NHBH_2C(O)OH$ comprises allowing a Lewis base adduct of $BH_2CO_2H$, such as a primary, secondary or tertiary amine, a heterocyclic amine, an aryl phosphine, capable of being displaced by the displacing amine, to react exclusively with a stoichiomeric excess of the displacing Lewis base at a temperature of 20° to 60° C. More particularly, the preferred Lewis base adduct compounds of $BH_2CO_2H$ contemplated within the scope of the present invention are tri-lower alkyl amines wherein each alkyl group contains 1 to 7 carbon atoms such as trimethyl amine, triethyl amine, and tri-n-propyl amine.

DESCRIPTION OF THE PREFERRED EMBODIMENTS

The process of preparing the novel amine-carboxyboranes and their utilities are more fully illustrated in the following discussion and examples. The relative amounts of the reactants mentioned herein are in parts by weight and room temperature includes the temperature range of 20°–60° C., say 50° to 60° C.

EXAMPLE I

Ammonia-carboxyborane ($H_3N.H_2BC(O)OH$)
Descriptive Discussion-(Synthesis, X-Ray Crystal Structure, and Biological Activity of Ammonia-carboxyborane, the Boron Analogue of Glycine)

The boron analogue of glycine, ammonia-carboxyborane ($H_3N.BH_2CO_2H$), was prepared by an amine displacement reaction on $Me_3N.BH_2CO_2H$, and structurally characterized by single-crystal x-ray analysis; biological assays indicate that this compound is biologically active, in particular it has been shown to possess significant antihyperlipidemic activity.

Glycine, $H_2NCH_2CO_2H$ or $H_3^{\oplus}NCH_2CO_2^{\ominus}$, may be considered the simplest alpha-amino acid and was the first to be discovered. We have now discovered the synthesis nd characterization of its isoelectronic and isosteric (protonated) boron analogue, ammonia-carboxyborane, $H_3N.BH_2CO_2H$ referred to in Table 1 as Compound 1. This compound may be viewed as the parent of a novel class of boron analogues of the common alpha-amino acids. Although we have previously reported the synthesis of other amine-carboxyboranes, e.g. $Me_3N.BH_2CO_2H$, the boron analogue of betaine in the *Journal of America Chemical Society*, Vol. 98, page 5703 (1976), all previous examples did not contain hydrogen bonded directly to nitrogen. An extremely important feature of the present example, like its glycine counterpart, is its potential to form peptide linkages and to be incorporated into proteins. The structure of Compound 1 has been unequivocally established by single-crystal x-ray analysis and its stability in several media investigated. Preliminary testing of Compound 1 in animal model studies has demonstrated biological activity, in particular, significant antihyperlipidemic activity.

Preparation of ammonia-carboxyborane was achieved by an amine exchange reaction. One part of $Me_3N.BH_2CO_2H$ was allowed to react with 10 parts liquid $NH_3$ in an evacuated stainless steel cylinder at room temperature for 3 weeks after which time excess ammonia was allowed to evaporate off and removed finally by pumping out. The residue was transferred to a flask with the aid of dry $CHCl_3$, refluxed for 3–4 hours, filtered hot, and washed with hot $CHCl_3$ to give $H_3N.BH_2CO_2H$ as an insoluble residue. This procedure led to a yield of crude product in the 50–55% range which remained essentially constant even when the time of reaction was increased from 3 to 6 weeks; a reaction period of 2 weeks gave $H_3N.BH_2CO_2H$ in 30% yield. When the crude product is freshly crystallized from cold water it melts at 116° C. but this is lowered, with no observable change in spectral characteristics, after storage of the product in screw-capped vials over a period of time in normal laboratory conditions. I.r. (KBr in $cm^{-1}$): nu (NH), a broad envelope with peaks at 3330 s, 3250 s, 3200 b, s; nu (OH) 3000 b; nu (NH . . . O) 2780 b, s, 2650 s; nu (BH) 2400 s, 2340 sh, 2250 sh; (delta+tau) (NH) 2050 w, 1840 b, w, 1760 b, w; nu (CO) 1640 s, delta (NH) 1650 s. The alphabetical symbols as used above and throughout the specification are defined as follows: s—absorption; b—broad absorption; sh—shoulder absorption and w—weak absorption.

Single-crystal x-ray analysis established the structure of ammonia-carboxyborane unequivocally. Monoclinic crystals of ammonia-carboxyborane belong to space group $P2_1/c$, with $a=4.859(2)$ Å, $b=5.291(2)$ Å, $c=15.523(7)$ Å beta$=108.42(3)°$, $U=378.6$ Å$^3$, $Z=4$, $d_c=1.313$ g. $cm^{-3}$. The structure was solved by direct methods using the MULTAN progrtam package as described G. Germain, et al., *Acta Crystallogr.*, Section A, Vol. 27, page 368. Full-matrix least-squares refinement of atomic positional and thermal (anisotropic B, C, N, O; isotropic H) parameters converged to an $R^4$ value of 0.052 over 598 statistically significant [I greater than 2.0 sigma (I)] reflections measured on an Enraf-Nonius CAD-3 automated diffractometer (Ni-filtered Cu-K alpha radiation, lambda$=1.5418$ Å; theta-2 theta scans). Although molecules of $H_3N.H_2BC(O)OH$ exist in the solid state in a form typical of optically inactive or racemic carboxylic acids, i.e. as centrosymmetric dimers, they have a slightly longer, and thus weaker, O-H . . . O hydrogen bonded distance [O . . . O 2.668(2) Å in $H_3N.H_2BC(O))H$ vs. ca. 2.64 Å in simple acids]. Dimers of $H_3N.H_2BC(O)OH$ are further associated via interdimer N-H . . . O hydrogen bonds [N . . . O 2.981 and 3.157 Å] involving two of the amino hydrogen atoms, a class of relatively strong intermolecular interactions not available to simple carboxylic acids, and a feature which must be partly responsible for the elevated melting point of $H_3H.H_2BC(O)OH$ compared to propionic acid ($-20.8°$ C.).

Hydrolysis of $H_3N.H_2BC(O)OH$ occurs very slowly as manifested by the observation that a 0.118M solution thereof in water underwent only trace decomposition in 3 hours. Very slow decomposition of $H_3N.H_2BC(O)OH$ also took place in alkali e.g. a 0.126M solution thereof in 1N NaOH underwent only 0.33% decomposition in 3 hours, with tapering off after that time, only trace amounts of gas being evolved in the following 3 days. In contrast, $H_3N.H_2BC(O)OH$ is readily hydrolyzed in acid, e.g. a 2.23:1 mole ratio of gas to $H_3N.H_2BC(O)OH$ was evolved after 3.5 hours from a 0.126M solution of $H_3N.H_2BC(O)OH$ in 1N HCl, and this increased to 2.27 after 20.5 hours by which time gas evolution was complete. Assuming that only hydrolysis of the B-H bonds occurs, a total of two moles of $H_2$ per mole of $H_3N.H_2BC(O)OH$ would be anticipated. However, i.r. analysis of the evolved gas showed that it contained CO, a fact which may be indicative of the involvement of a carbonyl intermediate $[H_3N.BH_2CO]^{\oplus}$ which could undergo subsequent hydrolysis to yield CO and $H_2$. That compound ammonia-carboxyborane ($H_3N.H_2BC(O)OH$) is reasonably thermally stable was demonstrated by heating 0.778 mmol $H_3N.H_2BC(O)OH$ in an evacuated flask at 60° C. for 8 hours when only 0.55 mole % was found to be decomposed.

Significant antitumor activity was observed following the procedures described by C. Piantadosi, et al. in the *Journal Pharm. Sci.*, Vol. 58, page 821 (1969). The control in this screen, 6-mercaptopurine, showed 99% inhibition. Additionally, significant antihyperlipidemic activities were found. Serum cholesterol was assayed by means of the Lieberman-Burchard reaction. The control in this assay, clofibrate, which requires 300 mg/kg for significant antihyperlipidemic activity, showed 98% inhibition. In each of the tests evaluating the antitumor and antihyperlipidemic activities a dose of 20 mg/kg per day of $H_3N.H_2BC(O)OH$ was administered to $CF_1$ male mice; the $LD_{50}$ is greater than 0.2 grams/kg. In the Ehrlich Ascites screen, inhibition of tumor growth was 76.5% for $H_3H.H_2BC(O)OH$, while lowering of the serum cholesterol level was 44% after 9 days and 60% after 16 days.

EXAMPLE II

Dimethylamine-carboxyborane $((CH_3)_2NH.H_2BC(O)OH$ Descriptive Discussion—(Synthesis, X-Ray Crystal Structure, and Antitumor Activity of Dimethylamine-carboxyborane, the Boron Analogue of N,N-Dimethylglycine)

The biologically active boron analogue of N,N-dimethylglycine, $Me_2NH.BH_2COOH$, was prepared by an amine displacement reaction on $Me_3N.BH_2COOH$ and has been structurally characterized by single-crystal x-ray analysis.

Preparation of dimethylamine-carboxyborane was achieved by the interaction of 10 parts dimethylamine with 1 part of trimethylamine-carboxyborane $(CH_3)_3N.BH_2C(O)OH)$ in a steel bomb at room temperature for a period of 15 days. Unreacted trimethylamine-carboxyborane was removed by dissolution in $CHCl_3$ at room temperature, leaving dimethylamine-carboxyborane which could be recrystallized from hot $CHCl_3$. Yields of dimethylamine-carboxyborane up to 80% can be obtained by extended reaction. Satisfactory analytical data were obtained; m.p. 105° C. (decomp.); nu (Nujol) NH 3220(sh); OH 3160; BH 2370(s), 2290(m); CO 1640(s) $cm^{-1}$; delta ($NMe_2$): 2.45 ppm in $D_2O$, taking delta (HOD)$=4.70$ ppm as reference. The structure was confirmed unequivocally by single-crystal x-ray analysis.

Crystal data: $C_3H_{10}BNO$, $M=102.93$, monoclinic, space group $P2_1/c$, $a=10.548(5)$, $b=6.600(3)$, $c=9.395(5)$ Å, beta$=90.98(5)°$, $U=654.0$ Å$^3$, $Z=4$, $D_c=1.045$ g. $cm^{-3}$. Intensity data to theta 67° were recorded on an Enraf-Nonius CAD-3 automated diffractometer (Ni-filtered Cu-$K_{alpha}$ radiation, lambda$=1.5418$ Å; theta-2 theta scans). The structure was solved by direct methods. Atomic positional and thermal parameters (anisotropic B, C, N, O; isotropic H) were refined by full-matrix least-squares calculations to R 0.066 over 885 statistically significant reflections. In the crystal the dimers are further associated through N-H . . . O hydrogen bonding (N . . . O 2.867 Å).

Although dimethylamine-carboxyborane is stable in air, the m.p. loses its sharpness when it is kept in normal laboratory conditions for a long time; other spectroscopic properties remain the same. It is also thermally quite stable; when heated in an evacuated flask at 60° C. for 8 hours, it partly sublimed with only ca. 0.7% evolution of $H_2$. The considerable hydrolytic stability of dimethylamine-carboxyborane was demonstrated by the fact that a ca. 0.05M solution thereof in $H_2O$ produced only ca. 1.5% of the theoretical amount of $H_2$ after 2 days (assuming complete decomposition to $H_2$), ca. 2.0% in one week, and 4.4% in three weeks. Moreover, dimethylamine-carboxyborane was found to be stable in strong base as no measureable amount of $H_2$ was evolved in 7 days from a ca. 0.06M solution thereof in 1N NaOH. On the other hand, however, dimethylamine-carboxyborane is readily hydrolyzed by 1N HCl as indicated by the liberation of more than the theoretical amount of gas within 2 days; the i.r. spectrum of the generated gas showed that carbon monoxide (CO) had been liberated in addition to $H_2$. Evolution of CO in this case may be indicative of a second reaction pathway with acid according to equation (1). The intermediate, $[Me_2NHBH_2CO]^\oplus$,

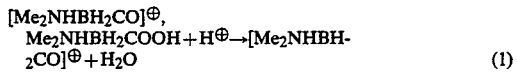

(1)

could undergo subsequent hydrolysis to give CO and $H_2$ in a manner similar to the reported hydrolysis of $BH_3CO$.

In the Ehrlich Ascites antitumor screen, dosages of 33.3 mg/kg per day of dimethylamine-carboxyborane into $CF_1$ male mice resulted in inhibition of tumor growth of 94.6%; the $LD_{50}$ for this compound is in excess of 200 mg/kg.

EXAMPLE III

Methylamine-carboxyborane ($CH_3NH_2.H_2BC(O)OH$) Descriptive Discussion—(Synthesis, X-Ray Crystal Structure, and Biological Activity of Methylamine-carboxyborane, the Boron Analogue of Sarcosine)

The boron analogue of sarcosine (N-methylglycine), $MeNH_2.BH_2COOH$, was prepared by an amine displacement reaction on $Me_3N.BH_2COOH$, and structurally characterized by single-crystal x-ray analysis; biological assays indicate that this compound has significant antitumor and antihyperlipidemic as well as moderate antiinflammatory activity.

The existence of a class of isoelectronic and isosteric boron containing alpha-amino acid analogues possessing biological activity would be expected to have considerable impact on many scientific and medical fields. Directed towards our goal of synthesizing boron analogues of the common alpha-amino acids, we have discovered the synthesis, x-ray crystal structure, and biological activity of methylamine-carboxyborane, $MeNH_2.BH_2COOH$, the boron analogue of sarcosine (N-methylglycine).

Preparation of methylamine-carboxyborane was achieved by the interaction of 10 parts of methylamine with 1 part $Me_3N.BH_2COOH$ in a stainless steel bomb at room temperature for 15 days. The unreacted trimethylamine-carboxyborane was removed by dissolution in hot $CHCl_3$, leaving methylamine-carboxyborane which could be recrystallized from cold $H_2O$; the yield before recrystallization was more than 95%. Satisfactory analytical data were obtained: m.p. 108°–109° C. (decomposed); i.r. (KBr in $cm^{-1}$) 3270 s and 3190 s $nu_{NH}$, 3040 s $nu_{OH}$, 1640 s $nu_{CO}$, 1600 s $delta_{NH}$; $^1$H NMR ($D_2O$) delta 2.3 ($CH_3N$) 4.7 (s HCO); mass spectrum m/e 89 ($M^+$, $C_2H_8{}^{11}BNO_2$).

Single-crystal x-ray analysis established the structure of methylamine-carboxyborane unequivocally. Monoclinic crystals of methylamine-carboxyborane belong to space group $P2_1/c$, a=5.125(2), b=5.509(3), c=17.289(8) Å, beta=99.91(5), U=481 Å, Z=4, $d_c$=1.228 g $cm^{-3}$. The structure was solved by direct methods disclosed in the article by G. Germain, et al. cited above. Full-matrix least-squares refinement of atomic positional and thermal (anisotropic B, C, N, O; isotropic H) parameters converged to an R value of 0.039 over 690 statistically significant (I greater than 2.0 sigma (I)) reflections measured on an Enraf-Nonius CAD-3 automated diffractometer (Ni-filtered Cu-K$_{alpha}$ radiation, lambda=1.5418 Å; theta-2 theta scans). The conformation and molecular dimensions of the centrosymmetric dimers were found in the solid state. As with trimethylamine-carboxyborane the intradimer hydrogen bonded O . . . O separation at 2.688 Å in methylamine-carboxyborane is slightly longer than the corresponding value of ca 2.64 Å which is found in simple carboxylic acids. The dimers are further associated in the crystal by weak N-H . . . O hydrogen bonds (N . . . O 3.101 and 3.102 Å).

Compound methylamine-carboxyborane proved to be fairly stable in air as evidenced by the fact that although prolonged exposure to normal laboratory conditions resulted in a slight lowering of the m.p., the i.r. spectrum remained unchanged. In water, slow decomposition of methylamine-carboxyborane occurred; typically, a 0.0443M solution thereof in water produced ¼% of the theoretical amount of $H_2$ after 3 hours (assuming complete decomposition to $H_2$), 1.7% in 21 hours, 2.4% in 7 days, and 2.9% in 14 days. Slow decomposition of methylamine-carboxyborane also took place in 1N NaOH solution; a 0.0423M solution thereof in 1N NaOH liberated no gas in 3 hours, 0.25% of H in 18 hours, and 0.85% in 7 days. In contrast to its relative stability in water and NaOH solution, methylamine-carboxyborane is sensitive to acid. Rapid decomposition of methylamine-carboxyborane in 1N HCl was accompanied by the generation of greater than the theoretical amount of $H_2$ in 24 hours; the i.r. spectrum of the generated gas showed that carbon monoxide (CO) was liberated in addition to $H_2$. Evolution of carbon monoxide may be indicative of a reaction pathway with acid whereby formation of the intermediate $[MeNH_2BH_2CO]^\oplus$ is followed by its hydrolysis to yield CO and $H_2$ in a manner similar to the reported hydrolysis of $BH_3CO$. Methylamine-carboxyborane is thermally fairly stable; on heating a sample thereof in an evacuated flask at 60° C. for 8 hours, only 0.6 mole % evolution of $H_2$ was observed.

Significant antitumor and antihyperlipidemic activities were demonstrated when dosages of 20 mg/kg per day of methylamine-carboxyborane were administered to $CF_1$ male mice; the $LD_{50}$ is greater than 1 g/kg. In the Ehrlich Ascites screen, inhibition of tumor growth was 94% for methylamine-carboxyborane, while lowering of the serum cholesterol level was 34% after 9 days and 33% after 16 days. Moderate antiinflammatory activity (46% inhibition by a dosage of 20 mg/kg of methylamine-carboxyborane) was also indicated.

The following comparative experimental example demonstrates that the attempted preparation of MeNH$_2$BH$_2$CO$_2$H using the method described by Spielvogel, et al. (in U.S. Pat. No. 4,368,194) yields no MeNH$_2$BH$_2$CO$_2$H. Using this method, only boric acid is produced.

COMPARATIVE EXPERIMENTATION

EXAMPLE IV

Attempted Hydrolysis of MeNH$_2$BH$_2$C(O)NHEt to Give MeNH$_2$BH$_2$COOH

Methylamine-N-ethylcarbamoylborane (0.10 g) was taken in 0.3N hydrochloric acid (10 ml) and heated at reflux for 7¼ hours. The solvent was removed under reduced pressure to give a white solid. $^{11}$B NMR(D$_2$O): delta=19.96 ppm, br. s. (H$_3$BO$_3$). No peaks corresponding to the starting material or the desired product were observed in the $^{11}$B NMR.

To summarized the experiment setforth in Example IV, the attempted preparation of MeNH$_2$BH$_2$CO$_2$H from MeNH$_2$BH$_2$C(O)N(Et)H by method of Spielvogel, et al. (U.S. Pat. No. 4,368,194, issued Jan. 11, 1983).

SUMMARY

MeNH$_2$BH$_2$C(O)N(Et)H was prepared by amine exchange on Me$_3$NBH$_2$C(O)N(Et)H (Spielvogel, et al., *Inorg., Chem.* 1984, 23, 1776; U.S. Pat. No. 4,587,359). This compound cannot be isolated using prior art disclosed in U.S. Pat. No. 4,368,194.

MeNH$_2$BH$_2$C(O)N(Et)H was refluxed with 0.3N HCl for 7¼ hours according to procedure of Spielvogel, et al. The solvent was removed under reduced pressure to give a white solid material. The $^{11}$B NMR in D$_2$O gave only a large signal for one species: delta=19.96 ppm, broad singlet (H$_3$BO$_3$). No peaks corresponding to the desired product (MeNH$_2$BH$_2$CO$_2$H, delta=−14.8 ppm) were observed and none for the starting material. Thus, the amide has completely decomposed into boric acid.

EXAMPLE V

Attempted Preparation of MeNH$_2$BH$_2$CO$_2$H by Method Described by Hall, et al. (J. Pharm. Sci. 68, 685 (1979)

Triethyloxonium tetrafluoroborate (25.3 ml of 19M solution in CH$_2$Cl$_2$) and methylamine-cyanoborane (1.95 g, 0.028 mole) were taken in a 100 ml r.b. flask fitted with a reflux condenser, and N$_2$ inlet. The solution was heated at reflux under N$_2$ for 24 hours. The solution was cooled and the solvent was removed under reduced pressure to give a thick yellow liquid: $^{11}$B NMR(CDCl$_3$, (CD$_3$)$_2$CO): delta=5.01 ppm, br., s; 0.17 ppm, s; −0.85 ppm, s; −22.85 ppm, t; JB,H=100±Hz. To this yellow oil 0.20 ml water was added and it was stirred at r.t. for 2½ days. The aqueous solution was repeatedly extracted with CH$_2$Cl$_2$. The organic extracts were dried (Na$_2$SO$_4$), filtered and the solvent was removed under reduced pressure to give a small amount (100 mg) of yellow liquid: $^{11}$B NMR(CDCl$_3$) delta=−0.09 ppm, quartet, J=15 Hz (small amount); −0.93 ppm, singlet, MeNH$_2$BF$_3$. The water was removed from the aqueous layer at room temperature to give a yellow liquid: $^{11}$B NMR(D$_2$O): delta=15.2 ppm, br. singlet, H$_3$BO$_3$; 1.36 ppm, quartet, J=15 Hz; −0.34 ppm, singlet, MeNH$_2$BF$_3$.

To summarize the experiment set forth in Example V, the attempted preparation of MeNH$_2$BH$_2$CO$_2$H according to Hall, et al. *J. Pharm. Sci.*, 68, page 685 (1979).

SUMMARY

MeNH$_2$BH$_2$CN was alkylated with Et$_3$O$^⊕$BF$_4$$^⊖$ to form MeNH$_2$BH$_2$$^⊕$CNEtBF$_4$$^⊖$ following the procedure of Hall, et al. The alkylated product was then stirred with water for 2½ days. The aqueous solution was repeatedly extracted with CH$_2$Cl$_2$. After drying and removal of solvent a small amount of yellow liquid was obtained. The $^{11}$B NMR of this sample gave two signals for two species, delta=−0.93 ppm, single (MeNH$_2$BF$_3$); delta=−0.09 ppm, quartet, J=15 Hz (unknown). $^{11}$B for authentic sample of MeNH$_2$BH$_2$CO$_2$H; delta=−14.8 ppm triplet, J=95.0 Hz. Thus this fraction did not yield the product. The aqueous phase was evaporated at room temperature to give a yellow liquid. The $^{11}$B NMR of this sample gave signals for three species: delta=15.2 ppm broad singlet (H$_3$BO$_3$); delta=1.36 ppm, quartet, J=15 Hz (unknown); delta=−0.34 ppm, singlet (MeNH$_2$BF$_3$). Again there was no signal for MeNH$_2$BH$_2$CO$_2$H. The observation of H$_3$BO$_3$ indicates that all boron hydride bonds have undergone hydrolysis. We conclude that the method of Hall, et al. will not yield any MeNH$_2$BH$_2$CO$_2$H.

TABLE 1

| Compound | Ehrlich Ascites % Inhibition | Antiinflammatory % Inhibition | Serum Cholesterol % Inhibition | LD$_{50}$ mg/kg |
|---|---|---|---|---|
| 1. NH$_3$BH$_2$C(O)OH | 76.5 | 16 | 60 | greater than 200 |
| 2. (CH$_3$)$_2$NHBH$_2$C(O)OH | 94.6 | 9 | 37 | greater than 200 |
| 3. CH$_3$NH$_2$BH$_2$C(O)OH | 93.7 | 46 | 34 | greater than 1000 |
| Dosage | 20 mg/kg/day | 20 mg/kg[1] | 20 mg/kg/day | |

NOTE:
The above table compares the relative activity of compounds 1 to 3 as an antitumor, and antiinflammatory agents or a cholesterol inhibiting agent.
[1]This dose is administered twice prior to the injection of the inflammatory causing agent.

TABLE 2

| Compound | Ehrlich Ascites % Inhibition | Serum Cholesterol % Inhibition 20 mg/kg/day | Serum Triglyceride % Inhibition 20 mg/kg/day |
|---|---|---|---|
| Me$_3$NBH$_2$CO$_2$H | 82 | 49 | 39 |
| NH$_3$BH$_2$CO$_2$H | 77 | 56 | 0.0 |
| MeNH$_2$BH$_2$CO$_2$H | 94 | 34 | 45 |

TABLE 2-continued

| Compound | Ehrlich Ascites % Inhibition | Serum Cholesterol % Inhibition 20 mg/kg/day | Serum Triglyceride % Inhibition 20 mg/kg/day |
| --- | --- | --- | --- |
| $Me_2NHBH_2CO_2H$ | 95 | 37 | 23 |

NOTE:
In the above table, it will be noted that the prior art exhibits biological properties which are not suggestive of those properties exhibited by the compositions of this invention.

We claim:

1. A compound of the formula $R_1R_2NHBH_2C(O)OH$ wherein $R_1$ is hydrogen or methyl and $R_2$ is selected from the group consisting of hydrogen and alkyl containing 1 to 18 carbon atoms, said compound being sufficiently pure to give results on single-crystal x-ray analysis which unequivocally confirms its structure.

2. A compound of the formula $R_1R_2NHBH_2C(O)OH$ wherein $R_1$ and $R_2$ are selected from the group consisting of hydrogen, methyl, ethyl, i-propyl, n-propyl, t-butyl, sec-butyl and n-butyl.

3. The compound of claim 2 wherein $R_1$ and $R_2$ are hydrogen.

4. The compound of claim 2 wherein $R_1$ and $R_2$ are methyl.

5. The compound of claim 2 wherein $R_1$ is hydrogen and $R_2$ is methyl.

* * * * *